United States Patent
Koktzoglou et al.

(10) Patent No.: US 10,401,459 B2
(45) Date of Patent: Sep. 3, 2019

(54) SYSTEMS AND METHODS FOR IMAGING VASCULAR CALCIFICATIONS WITH MAGNETIC RESONANCE IMAGING

(71) Applicant: NORTHSHORE UNIVERSITY HEALTH SYSTEM, Evanston, IL (US)

(72) Inventors: Ioannis Koktzoglou, Des Plaines, IL (US); Robert R Edelman, Highland Park, IL (US)

(73) Assignee: NORTHSHORE UNIVERSITY HEALTH SYSTEM, Evanston, IL (US)

( * ) Notice: Subject to any disclaimer, the term of this patent is extended or adjusted under 35 U.S.C. 154(b) by 730 days.

(21) Appl. No.: 14/872,611

(22) Filed: Oct. 1, 2015

(65) Prior Publication Data
US 2017/0097402 A1    Apr. 6, 2017

(51) Int. Cl.
*G01V 3/00* (2006.01)
*G01R 33/565* (2006.01)
*G01R 33/48* (2006.01)
*A61B 5/055* (2006.01)

(52) U.S. Cl.
CPC ........ *G01R 33/56527* (2013.01); *A61B 5/055* (2013.01); *G01R 33/4824* (2013.01); *G01R 33/4828* (2013.01)

(58) Field of Classification Search
CPC .... H05K 1/021; H05K 1/0272; H05K 1/0206; H05K 2201/064; H05K 2201/10416; G01R 33/5607; G01R 33/5615; G01R 33/5635; G01R 33/34; G01R 33/4804; G01R 33/4824; A61B 5/055; A61B 5/7285

USPC .......................................................... 324/322
See application file for complete search history.

(56) References Cited

U.S. PATENT DOCUMENTS

| | | | | |
|---|---|---|---|---|
| 8,588,890 B2* | 11/2013 | Kimura | .................. | G01R 33/56 324/306 |
| 2009/0185981 A1* | 7/2009 | Karczmar | .............. | A61B 5/055 424/9.3 |
| 2014/0100443 A1* | 4/2014 | Koktzoglou | ......... | A61B 5/7285 600/413 |
| 2015/0196223 A1* | 7/2015 | Koktzoglou | ........... | A61B 5/055 600/410 |

(Continued)

OTHER PUBLICATIONS

Cai, et al., Classification of Human Carotid Atherosclerotic Lesions With In Vivo Multicontrast Magnetic Resonance Imaging, Circulation, 2002, 106:1368-1373.

(Continued)

Primary Examiner — Rodney E Fuller
(74) Attorney, Agent, or Firm — Quarles & Brady LLP

(57) ABSTRACT

Systems and methods for acquiring magnetic resonance images that accurately depict vascular calcifications, or other objects composed of magnetic susceptibility-shifted substances, in a subject are provided. The images are generally acquired using a pulse sequence that is designed to reduce physiological motion-induced artifacts and to mitigate chemical-shift artifacts from water-fat boundaries. Advantageously, the MRI technique described here suppresses chemical-shift artifacts without significantly reducing the signal intensity from fatty tissues, and thereby allows for more reliable visualization of vascular calcifications.

20 Claims, 2 Drawing Sheets

(56) References Cited

U.S. PATENT DOCUMENTS

2015/0309137 A1* 10/2015 Bydder .............. G01R 33/4828
                                                          324/309
2017/0322274 A1* 11/2017 Bolster, Jr. ......... G01R 33/4824

OTHER PUBLICATIONS

Chan, et al., Ultra-short Echo Time Cardiovascular Magnetic Resonance of Atherosclerotic Carotid Plaque, Journal of Cardiovascular Magnetic Resonance, 2010, 12:17, 8 pages.

Edelman, et al., Projection MR Imaging of Peripheral Arterial Calcifications, Magnetic Resonance in Medicine, 2015, 73(5):1939-1945.

Koktzoglou, Gray Blood Magnetic Resonance for Carotid Wall Imaging and Visualization of Deep-Seated and Superficial Vascular Calcifications, Magnetic Resonance in Medicine, 2013, 70:75-85.

* cited by examiner

SYSTEMS AND METHODS FOR IMAGING VASCULAR CALCIFICATIONS WITH MAGNETIC RESONANCE IMAGING

BACKGROUND OF THE INVENTION

The field of the invention is systems and methods for magnetic resonance imaging ("MRI"). More particularly, the invention relates to systems and methods for rapid MRI of vascular calcifications and other magnetic susceptibility-shifted substances.

Vascular calcifications are a major component of atherosclerotic disease, and their presence is a risk factor for future cardiovascular morbidity and mortality. In clinical practice, computed tomography (CT) is used to visualize and quantify vascular calcifications. CT, however, involves the use of potentially harmful ionizing radiation and thus is not well-suited for longitudinal and/or serial assessments of atherosclerotic disease, or for screening in the general population.

MRI is a promising imaging modality for visualizing and quantifying vascular calcifications because it does not use ionizing radiation and thus does not have the safety concerns of CT. However, vascular calcifications generally appear dark in magnetic resonance images, and are often confounded by image artifacts, such as chemical-shift artifacts that appear at fat-water interfaces Chemical-shift artifacts are typically reduced by the application of frequency-selective radio frequency (RF) pulses tuned to the Larmor frequency of lipid spins. However, for the purpose of imaging vascular calcifications, it is important to maintain the bright signal from fat so as to contrast with the low signal from the vascular calcifications. Dixon-type techniques can eliminate chemical-shift artifacts by creating separate fat-only and water-only images; however, it is necessary to depict both water and fat together in a single image in order to provide optimal contrast with vascular calcifications.

Other approaches for imaging vascular calcifications that have been proposed fail to rapidly and accurately identify calcifications. So-called "multi-contrast" MRI, which includes acquiring a dark-blood T1-weighted fast spin echo (FSE) scan, a dark-blood T2-weighted FSE scan, a dark-blood spin-density weighted FSE scan, and a bright-blood time-of-flight (TOF) scan, is one such approach. This multi-contrast approach identifies vascular calcifications based on their dark appearance in all four acquisitions; however, the method requires long scan times associated with acquiring data using multiple (typically four) different scans, and thus is not a rapid technique. Accuracy in the multi-contrast technique also suffers due to poor spatial resolution (e.g., because the FSE techniques are typically 2D and not 3D techniques) and to arterial inhomogeneity and saturation artifacts in TOF imaging. Furthermore, interpretation of multiple image sets is complex and can be impossible due to patient motion in one or more scans.

Another approach for visualizing calcifications involves the use of 3D dark-blood acquisitions (either FSE or gradient-echo) that display the arterial wall. This approach does not allow for rapid and accurate identification because calcifications are visualized based on their dark appearance, but can be hard to distinguish from the many other structures within the imaging field that appear dark, including vascular lumen and perivascular fat. An offshoot technique referred to as "gray-blood imaging" addresses the poor contrast between superficial vascular calcifications and the vascular lumen, but does not solve the issue of poor contrast between perivascular fat and vascular calcifications.

Ultrashort echo time (UTE) MRI could potentially be used to visualize vascular calcifications by the subtracting the signal intensity of a long echo time (e.g., TE typically on the order of a few milliseconds) from that of an ultrashort echo time (e.g., TE significantly less than one millisecond). However, UTE methods are hindered by artifacts from gradient timing errors and poor spatial resolution. Experience with these methods has largely been limited to in-vitro imaging and it is unclear if these methods would work for in-vivo imaging of vascular calcifications despite the drawbacks noted above.

Two other methods for visualizing calcifications with MRI have recently been used. The first method includes using a non-selective 3D UTE sequence. Drawbacks of this method include long acquisition times and sensitivity to artifacts from physiologic motion (e.g., from breathing). The second method is a 3D Cartesian acquisition that uses an in-phase echo time. Drawbacks of this method include chemical shift artifacts in the frequency-encoding direction and sensitivity to physiologic motion.

Thus, there remains a need for MRI techniques that are capable of rapidly and accurately imaging vascular calcifications.

SUMMARY OF THE INVENTION

The present invention overcomes the aforementioned drawbacks by providing a method for producing an image that depicts vascular calcifications within a subject using a magnetic resonance imaging ("MRI") system. Data are acquired with the MRI system by controlling the MRI system to perform a pulse sequence in which the data are acquired by sampling k-space with a non-Cartesian trajectory. The data are acquired at an echo time that is selected such that water spins and fat spins are sufficiently in phase, thereby reducing chemical shift artifacts without significantly reducing signal from the fat spins. An image that depicts vascular calcifications is then reconstructed from the acquired data. Advantageously, acquiring the data by sampling k-space with a non-Cartesian trajectory blurs chemical shift artifacts in the reconstructed image without blurring the vascular calcifications.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for acquiring magnetic resonance images that accurately depict vascular calcifications, or other objects composed of magnetic susceptibility-shifted substances, in a subject. The images are generally acquired using a pulse sequence that is designed to reduce physiological motion-induced artifacts and to mitigate chemical-shift artifacts from water-fat boundaries. Advantageously, the MRI technique described here suppresses chemical-shift artifacts without reducing the signal intensity from fatty tissues, and thereby allows for more reliable visualization of vascular calcifications.

Described here are MRI pulse sequences that obtain images that conspicuously depict vascular calcifications and other magnetic susceptibility-shifted substances. In general, the pulse sequence can include a gradient-echo sequence that uses a non-Cartesian k-space sampling trajectory and an echo time selected such that fat and water spins are sufficiently in-phase so as to minimize chemical-shift artifacts at fat-water boundaries while still retaining significant image signal from fatty tissues. As one example, the non-Cartesian k-space sampling trajectory can be a radial k-space sampling trajectory. The use of radial, or other suitable non-Cartesian, k-space sampling trajectories eliminates chemical-shift artifacts, which can be mistaken for vascular calcifications or other magnetic susceptibility-shifted substances, by benignly blurring them in the image. While in general practice, blurring of any part of an image is considered a negative effect and thus to be avoided, the present innovation makes novel use of purposely blurring an image to eliminate visually distracting image artifacts.

The imaging method described here eliminates poor contrast between neighboring soft-tissues and other hypointense structures within the field-of-view associated with previous dark-blood MRI methods. The imaging method described here also eliminates artifacts and long acquisition times associated with ultrashort echo time techniques, and eliminates chemical-shift artifacts in the frequency-encoding direction observed with Cartesian trajectories. Furthermore, the use of radial sampling confers robustness against physiologic motion and flow-related artifacts. It should be noted that the imaging techniques described here are compatible with 2D and 3D acquisition strategies.

Figure 1:
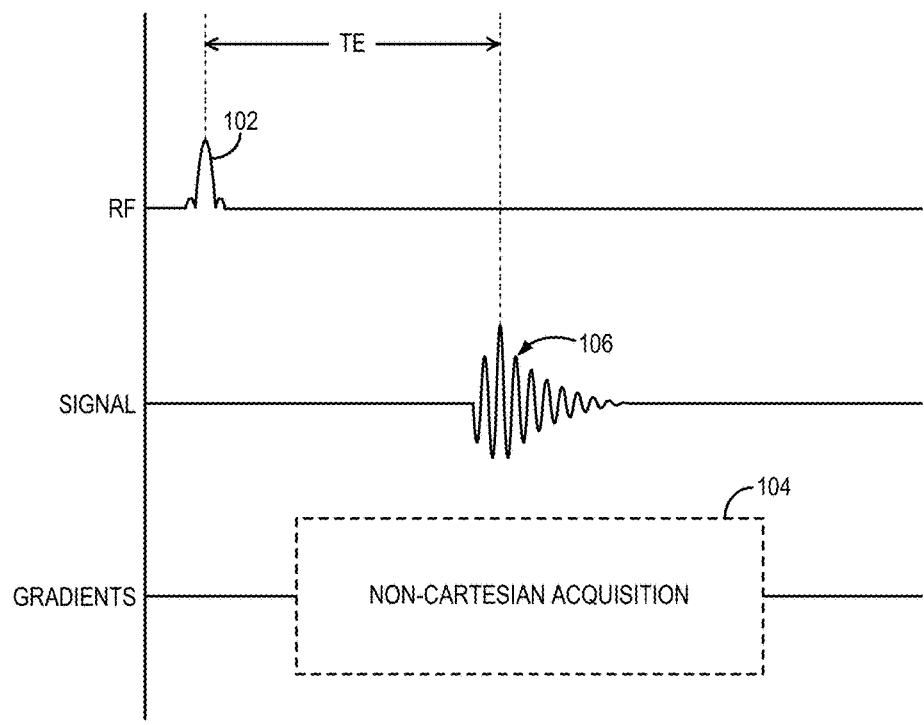
FIG. 1 is an example of a pulse sequence that can implement the present invention.

An example of a pulse sequence that may be employed to direct the MRI system to acquire image data in accordance with the present invention is illustrated in FIG. 1. Generally, the pulse sequence includes a radio frequency ("RF") excitation pulse 102 that is applied to a subject to generate transverse magnetization in an imaging volume located within that subject. The imaging volume can include one or more imaging slices, one or more imaging slabs, or a single imaging volume. In the instances where the imaging volume includes one or more imaging slices, the RF excitation pulse 102 is played out in the presence of an appropriate slice-selective gradient (not shown) in order to produce transverse magnetization in the prescribed imaging slice.

Following the application of the RF excitation pulse 102, a data acquisition sequence 104 is performed to acquire data from the subject, such as by forming and sampling a gradient echo 106. The data acquisition sequence 104 preferably samples k-space using a non-Cartesian trajectory. In one embodiment, the data acquisition sequence 104 includes a fast low-angle shot ("FLASH"), or spoiled gradient ("SPGR"), data acquisition that implements radial sampling of k-space. In other embodiments, however, the data acquisition sequence 104 can include other fast gradient echo sequences, and can implement non-Cartesian sampling trajectories other than radial trajectories.

The data acquisition sequence 104 is specifically designed to minimize chemical-shift artifacts at fat-water interfaces, which can otherwise mimic vascular calcifications. In addition to selecting a non-Cartesian k-space trajectory that benignly blurs chemical-shift artifacts, the an echo time of the pulse sequence is chosen such that water spins and fat spins are sufficiently in phase to reduce chemical-shift artifacts while still retaining significant image signal from fatty tissues. For example, an echo time can be chosen such that water spins and fat spins are $\pi/4$ radians (45 degrees) or less out of phase (i.e., there is a phase difference between water spins and fat spins of about zero to about $\pi/4$ radians). As another specific example, the echo time can be selected such that water spins and fat spins are in-phase.

Figure 2:
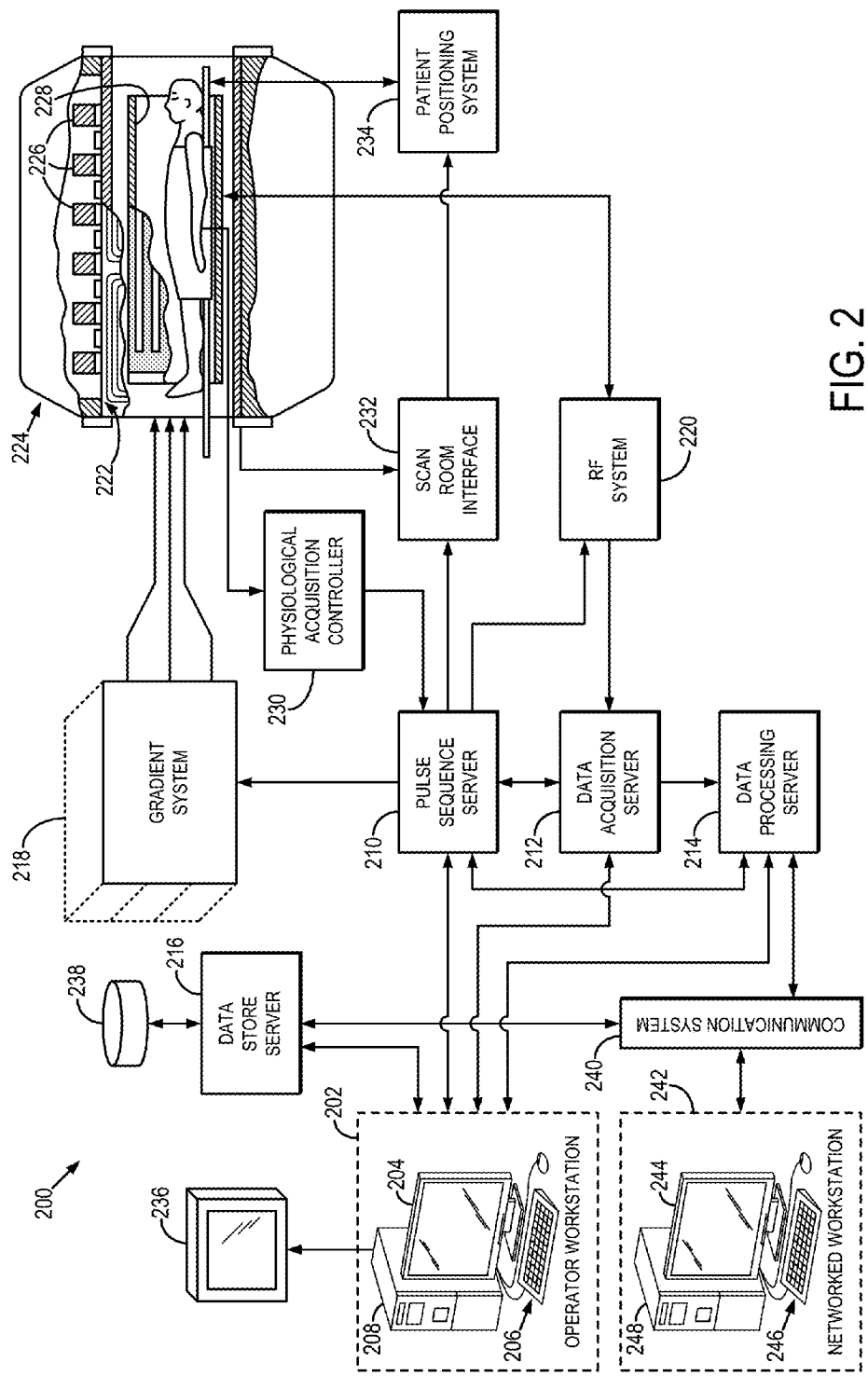
FIG. 2 is a block diagram of an example of a magnetic resonance imaging ("MRI") system.

Referring particularly now to FIG. 2, an example of a magnetic resonance imaging ("MRI") system 200 is illustrated. The MRI system 200 includes an operator workstation 202, which will typically include a display 204; one or more input devices 206, such as a keyboard and mouse; and a processor 208. The processor 208 may include a commercially available programmable machine running a commercially available operating system. The operator workstation 202 provides the operator interface that enables scan prescriptions to be entered into the MRI system 200. In general, the operator workstation 202 may be coupled to four servers: a pulse sequence server 210; a data acquisition server 212; a data processing server 214; and a data store server 216. The operator workstation 202 and each server 210, 212, 214, and 216 are connected to communicate with each other. For example, the servers 210, 212, 214, and 216 may be connected via a communication system 240, which may include any suitable network connection, whether wired, wireless, or a combination of both. As an example, the communication system 240 may include both proprietary or dedicated networks, as well as open networks, such as the internet.

The pulse sequence server 210 functions in response to instructions downloaded from the operator workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding magnetic resonance signals. The gradient coil assembly 222 forms part of a magnet assembly 224 that includes a polarizing magnet 226 and a whole-body RF coil 228.

RF waveforms are applied by the RF system 220 to the RF coil 228, or a separate local coil (not shown in FIG. 2), in order to perform the prescribed magnetic resonance pulse sequence. Responsive magnetic resonance signals detected by the RF coil 228, or a separate local coil (not shown in FIG. 2), are received by the RF system 220, where they are amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the scan prescription and direction from the pulse sequence server 210 to produce RF pulses of the desired frequency, phase, and pulse amplitude waveform. The generated RF pulses may be applied to the whole-body RF coil 228 or to one or more local coils or coil arrays (not shown in FIG. 2).

The RF system 220 also includes one or more RF receiver channels. Each RF receiver channel includes an RF preamplifier that amplifies the magnetic resonance signal received by the coil 228 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 210 also optionally receives patient data from a physiological acquisition controller 230. By way of example, the physiological acquisition controller 230 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, such that no data is lost by data overrun. In some scans, the data acquisition server 212 does little more than pass the acquired magnetic resonance data to the data processor server 214. However, in scans that require information derived from acquired magnetic resonance data to control the further performance of the scan, the data acquisition server 212 is programmed to produce such information and convey it to the pulse sequence server 210. For example, during prescans, magnetic resonance data is acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also be employed to process magnetic resonance signals used to detect the arrival of a contrast agent in a magnetic resonance angiography ("MRA") scan. By way of example, the data acquisition server 212 acquires magnetic resonance data and processes it in real-time to produce information that is used to control the scan.

The data processing server 214 receives magnetic resonance data from the data acquisition server 212 and processes it in accordance with instructions downloaded from the operator workstation 202. Such processing may, for example, include one or more of the following: reconstructing two-dimensional or three-dimensional images by performing a Fourier transformation of raw k-space data; performing other image reconstruction algorithms, such as iterative or back projection reconstruction algorithms; applying filters to raw k-space data or to reconstructed images; generating functional magnetic resonance images; calculating motion or flow images; and so on.

Images reconstructed by the data processing server 214 are conveyed back to the operator workstation 202 where they are stored. Real-time images are stored in a data base memory cache (not shown in FIG. 2), from which they may be output to operator display 202 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the operator workstation 202. The operator workstation 202 may be used by an operator to archive the images, produce films, or send the images via a network to other facilities.

The MRI system 200 may also include one or more networked workstations 242. By way of example, a networked workstation 242 may include a display 244; one or more input devices 246, such as a keyboard and mouse; and a processor 248. The networked workstation 242 may be located within the same facility as the operator workstation 202, or in a different facility, such as a different healthcare institution or clinic.

The networked workstation 242, whether within the same facility or in a different facility as the operator workstation 202, may gain remote access to the data processing server 214 or data store server 216 via the communication system 240. Accordingly, multiple networked workstations 242 may have access to the data processing server 214 and the data store server 216. In this manner, magnetic resonance data, reconstructed images, or other data may be exchanged between the data processing server 214 or the data store server 216 and the networked workstations 242, such that the data or images may be remotely processed by a networked workstation 242. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image that depicts vascular calcifications within a subject using a magnetic resonance imaging (MRI) system, the steps comprising:
   (a) selecting a pulse sequence that blurs chemical shift artifacts, wherein the pulse sequence is configured to acquire data from the subject using a non-Cartesian trajectory at an echo time selected such that water spins and fat spins are sufficiently in phase to reduce chemical-shift artifacts at fat-water boundaries while still retaining image signal from fatty tissues;
   (b) acquiring data with the MRI system by controlling the MRI system to perform the pulse sequence; and
   (c) reconstructing from the acquired data, an image that depicts vascular calcifications and minimizes the appearance of fat-water interfaces;
   wherein acquiring the data by sampling k-space with the non-Cartesian trajectory blurs chemical shift artifacts in the reconstructed image without blurring the vascular calcifications.

2. The method as recited in claim 1, wherein the non-Cartesian trajectory is a radial trajectory.

3. The method as recited in claim 1, wherein the echo time is selected such that a phase difference between water spins and fat spins is between zero and $\pi/4$ radians.

4. The method as recited in claim 3, wherein the echo time is selected such that water spins and fat spins are in phase.

5. A magnetic resonance imaging system, comprising:
   a magnet system configured to generate a polarizing magnetic field about at least a portion of a subject arranged in the MM system;
   a plurality of gradient coils configured to apply a magnetic field gradient to the polarizing magnetic field;
   a radio frequency (RF) system including an RF coil configured to apply an RF field to the subject and to receive magnetic resonance signals therefrom;
   a computer system programmed to:
      (a) select a pulse sequence that blurs chemical shift artifacts, wherein the pulse sequence is configured to acquire data from the subject using a non-Cartesian trajectory at an echo time selected such that water spins and fat spins are sufficiently in phase to reduce chemical-shift artifacts at fat-water boundaries while still retaining image signal from fatty tissues;
      (b) acquire the data by controlling the plurality of gradient coils and the RF system to perform the pulse sequence; and
      (c) reconstruct from the acquired data, an image that depicts vascular calcifications and minimizes the appearance of fat-water interfaces, wherein chemical shift artifacts are blurred in the reconstructed image without blurring the vascular calcifications as a result of acquiring the data by sampling k-space with the non-Cartesian trajectory.

6. The MRI system as recited in claim 5, wherein the non-Cartesian trajectory is a radial trajectory.

7. The MRI system as recited in claim 5, wherein the echo time is selected such that a phase difference between water spins and fat spins is between zero and $\pi/4$ radians.

8. The MRI system as recited in claim 7, wherein the echo time is selected such that water spins and fat spins are in phase.

9. A method for producing an image that depicts calcifications within a subject using a magnetic resonance imaging (MRI) system, the steps comprising:
   (a) acquiring data with the MRI system by controlling the MRI system to perform a pulse sequence selected to acquire data by sampling k-space with a non-Cartesian trajectory and an echo time configured to maintain water spins and fat spins sufficiently in phase and control chemical shift artifacts while still retaining image signal from fatty tissues; and
   (b) reconstructing from the acquired data, an image that depicts calcifications and minimizes the appearance of fat-water interfaces;
   wherein acquiring the data by sampling k-space with a non-Cartesian trajectory blurs chemical shift artifacts in the reconstructed image without blurring the calcifications.

10. The method as recited in claim 9, wherein the non-Cartesian trajectory is a radial trajectory.

11. The method as recited in claim 9, wherein the echo time is selected such that a phase difference between water spins and fat spins is between zero and $\pi/4$ radians.

12. The method as recited in claim 11, wherein the echo time is selected such that water spins and fat spins are in phase.

13. A magnetic resonance imaging system, comprising:
   a magnet system configured to generate a polarizing magnetic field about at least a portion of a subject arranged in the MM system;
   a plurality of gradient coils configured to apply a magnetic field gradient to the polarizing magnetic field;
   a radio frequency (RF) system including an RF coil configured to apply an RF field to the subject and to receive magnetic resonance signals therefrom;
   a computer system programmed to:
      (a) control the plurality of gradients and the RF system to perform a pulse sequence selected to acquire data by sampling k-space with a non-Cartesian trajectory at an echo time that maintains water spins and fat spins sufficiently in phase, thereby reducing chemical shift artifacts while still retaining image signal from fatty tissues; and
      (b) reconstruct from the acquired data, an image that depicts calcifications and minimizes the appearance of fat-water interfaces, wherein chemical shift artifacts are blurred in the reconstructed image without blurring the calcifications as a result of acquiring the data by sampling k-space with a non-Cartesian trajectory.

14. The MRI system as recited in claim 13, wherein the non-Cartesian trajectory is a radial trajectory.

15. The MRI system as recited in claim 13, wherein the echo time is selected such that a phase difference between water spins and fat spins is between zero and $\pi/4$ radians.

16. The MRI system as recited in claim 15, wherein the echo time is selected such that water spins and fat spins are in phase.

17. A method including steps comprising:
   (a) selecting a pulse sequence that blurs chemical shift artifacts, wherein the pulse sequence is configured to acquire data from the subject using a non-Cartesian trajectory at an echo time selected such that water spins and fat spins are sufficiently in phase to reduce chemical-shift artifacts at fat-water boundaries while still retaining image signal from fatty tissues and wherein;
   (b) acquiring data from a subject with the MRI system by controlling the MM system to perform the pulse sequence; and
   (c) reconstructing from the acquired data, an image that depicts the subject and minimizes the appearance of fat-water interfaces;
   wherein acquiring the data by sampling k-space with the non-Cartesian trajectory blurs chemical-shift artifacts in the reconstructed image.

18. The method as recited in claim 17, wherein the non-Cartesian trajectory is a radial trajectory.

19. The method as recited in claim 17, wherein the echo time is selected such that a phase difference between water spins and fat spins is between zero and $\pi/4$ radians.

20. The method as recited in claim 17, wherein the echo time is selected such that water spins and fat spins are in phase.

* * * * *

UNITED STATES PATENT AND TRADEMARK OFFICE
CERTIFICATE OF CORRECTION

PATENT NO.         : 10,401,459 B2
APPLICATION NO.    : 14/872611
DATED              : September 3, 2019
INVENTOR(S)        : Ioannis Koktzoglu et al.

It is certified that error appears in the above-identified patent and that said Letters Patent is hereby corrected as shown below:

In the Claims

Column 7, Claim 5, Line 6, "MM" should be --MRI--.

Column 8, Claim 13, Line 7, "MM" should be --MRI--.

Column 8, Claim 17, Line 44, "MM" should be --MRI--.

Signed and Sealed this
Fifteenth Day of October, 2019

Andrei Iancu
*Director of the United States Patent and Trademark Office*